(12) United States Patent
Deleris et al.

(10) Patent No.: US 9,409,278 B2
(45) Date of Patent: Aug. 9, 2016

(54) METHOD AND SYSTEM FOR THE PLY-BY-PLY MACHINING OF A COMPONENT MADE OF COMPOSITE MATERIAL, BY APPLYING ENERGY

(71) Applicant: JEDO TECHNOLOGIES, Labege (FR)

(72) Inventors: Michel Deleris, Rebigue (FR); François Cenac, Saintefoy d'Aigrefeuille (FR)

(73) Assignee: JEDO TECHNOLOGIES, Labege (FR)

( * ) Notice: Subject to any disclaimer, the term of this patent is extended or adjusted under 35 U.S.C. 154(b) by 0 days.

(21) Appl. No.: 14/394,775

(22) PCT Filed: Apr. 12, 2013

(86) PCT No.: PCT/EP2013/001066
§ 371 (c)(1),
(2) Date: Oct. 16, 2014

(87) PCT Pub. No.: WO2013/156124
PCT Pub. Date: Oct. 24, 2013

(65) Prior Publication Data
US 2015/0099422 A1    Apr. 9, 2015

(30) Foreign Application Priority Data

Apr. 20, 2012 (FR) ...................................... 12 53665

(51) Int. Cl.
| | | |
|---|---|---|
| B24C 1/04 | (2006.01) | |
| B29C 73/26 | (2006.01) | |
| B29C 73/10 | (2006.01) | |
| G01N 21/88 | (2006.01) | |
| G01N 21/84 | (2006.01) | |

(52) U.S. Cl.
CPC . *B24C 1/04* (2013.01); *B29C 73/26* (2013.01); *B29C 73/10* (2013.01); *B29C 2073/264* (2013.01); *G01N 21/8806* (2013.01); *G01N 2021/8438* (2013.01); *G01N 2021/8472* (2013.01)

(58) Field of Classification Search
CPC .......... B24C 1/04; B29C 73/26; B29C 73/10; B29C 2073/264; G01N 21/8806; G01N 2021/8438; G01N 2021/8472
USPC .......................................................... 451/2
See application file for complete search history.

(56) References Cited

U.S. PATENT DOCUMENTS 3,691,695 A * 9/1972 Green ...................... B28D 5/00
                                                          451/2
5,281,798 A    1/1994 Hamm
(Continued)

FOREIGN PATENT DOCUMENTS

DE          3702250       7/1988
WO    WO2011/018163       2/2011

*Primary Examiner* — George Nguyen
(74) *Attorney, Agent, or Firm* — Defillo & Associates, Inc; Evelyn A Defillo

(57) ABSTRACT

The invention relates to machine a component made of composite material in order to eliminate singularities, defects or damage to the component using a method that is repeatable and adaptable. To do this, it is proposed that the defects and their type be identified by image processing of the surface of the component and that the local machining rates at which the plies are machined be regulated at the function of this identification. According to one embodiment, a system (10) for the ply-by-ply machining of defects of a component made of composite material includes a numerical data processing unit (1) combined with a sweep control (2) that commands the sweep of a high-pressure water jet machine (20), and an image formation assembly (3) including an image capturing device (30, 31) connected with the numerical processing unit (1). The processing unit (1) includes regulating devices (11, 13) indexing local sweep rates, by convergence of brightness levels (NB) from the successive sweeps, these being formed by the image capturing assembly (3) toward making the brightness uniform according to a model (Mr) correlating brightness to ply state typology identification (BT) that can be supplied by a library (4). The correlation data (BT) and brightness levels (NB) are stored in memory modules (12, 14) of the processing unit (1).

12 Claims, 4 Drawing Sheets

(56) References Cited

U.S. PATENT DOCUMENTS

| | | | | |
|---|---|---|---|---|
| 5,423,713 A * | 6/1995 | Mishima | ............... | B24C 3/322 451/102 |
| 6,347,976 B1 * | 2/2002 | Lawton | ............... | B08B 7/0035 451/38 |
| 7,585,201 B2 * | 9/2009 | Kanai | ............... | B24C 1/00 451/2 |
| 8,485,861 B2 * | 7/2013 | Boyden | ............... | A61K 9/0019 451/102 |
| 2010/0316458 A1 | 12/2010 | Lindgren | | |

* cited by examiner

METHOD AND SYSTEM FOR THE PLY-BY-PLY MACHINING OF A COMPONENT MADE OF COMPOSITE MATERIAL, BY APPLYING ENERGY

CROSS REFERENCE TO RELATED APPLICATION

This application is a national stage entry of PCT/EP2013/001066 filed Apr. 12, 2013, under the International Convention, claiming priority over FR 1253665 filed Apr. 20, 2012.

TECHNICAL FIELD

The invention relates to a method for the ply-by-ply machining of components made of composite material, in the context of use in any machining process in which the appropriate amount of energy is applied to remove a given volume of material, particularly by means of a high-pressure water jet. The invention also relates to an optimization system adapted to use this method.

The invention is applicable to panels of storage holds, frames or walls, intended particularly, but not exclusively, for the aeronautics industry. The invention relates particularly, but not exclusively, to the repair of these panels. It is also applicable to the shape machining of these panels with constant plies.

The composite material is generally composed of a stack of plies of resin-impregnated fibers, namely carbon, glass, Kevlar or equivalent fibers, oriented in different directions from one ply to the next. The plies are impregnated with a resin to form an assembly having high strength regardless of the orientation of the stresses.

However, these panels are particularly exposed, and may be subject to shock, particularly in the form of ground impact, or malformation caused during production. These defects extend in the plies and their repair is particularly important in view of the mechanical strength imparted by these structures.

There are several methods for making repairs. In a conventional method, the damaged area is reinforced by a bonded and riveted metal plate. This method is fast, but has the major drawback of creating turbulence, thus giving rise to defective air flow and consequently aerodynamic disturbances, because the applied part has a different geometry and changes the aerodynamic design.

PRIOR ART

In a more advanced method, the material around the damaged area is removed to form concentric steps or levels between the successive plies, using a system for applying energy, for example a pressurized water jet. The area recessed in this way is reconstructed by the polymerization of new plies having an appropriate geometry. The part made of composite repair material then mates with the contour of the edges of the recessed area.

This method requires a high degree of adaptability if it is not to be subject to stresses which cannot be quantified in advance, arising from singularities in the materials such as relaxation, ply drops (offsetting, etc.), the damage to be repaired, the variability in ply thickness (internal defects) or the presence of different materials.

In order to adapt the amount of material to be processed, the recess is generally formed by manual machining: uncured plies impregnated with epoxy resin are added ply by ply, and the resin is then hardened at ambient temperature or accelerated by heat treatment or other treatment depending on the nature of the resin.

However, this manual machining is difficult to reproduce and is highly time-consuming. Various processes have therefore been developed with the aim of automating this machining, such as abrasive water jets, lasers, cutting tools and ultrasound. Recesses are thus made in a guided way by constant depth machining operations. However, it is difficult to adapt these recesses to the aforementioned singularities.

The defects encountered in composite materials include the formation of "wrinkles" (as they are known in the English terminology): these wrinkles are caused by the formation of plies of variable thickness. Furthermore, internal stresses in composite materials created in the course of manufacture cause variations in the geometry of a component before, during and after machining.

These variations in geometry make it difficult to use shaping tools, such as conventional machining tools, because they require a precise knowledge of the geometry of the component.

DISCLOSURE OF THE INVENTION

The invention proposes to provide optimized ply-by-ply machining of composite components, which can automatically control a variable depth dependent on the singularities and other defects or damage, and can therefore provide constant ply machining. In other words, the invention proposes to provide adaptability of the amount of material to be removed while ensuring reproducibility of the machining with an automatic energy application system. For this purpose, it is proposed that the plies, the defects and their typology be identified by image analysis of the swept areas, and that the machining speed parameters be adjusted as a function of this identification, in order to eliminate defects by successive converging compensations of the ply machining in the swept areas.

More precisely, the present invention proposes a method of ply-by-ply machining of a component made of composite material, composed of a stack of plies, by application of energy in flows according to an area-by-area sweep of the component to be machined. In this method, the detection of at least one light flux reflected from the areas machined by sweeping the component provides local brightness levels correlated with ply orientations. At least one parameter controlling the variation of the depth of material to be machined is then indexed as a function of the plies of the component detected in the swept areas by their brightness level and their relative position with respect to an inter-ply interface level. The indexing is calibrated by predefined increments in a range including a reference value and correlated with degrees of depth of removal of material, so that the brightness levels of the sweeps converge toward uniform brightness when the ply is constant.

The term "swept areas" denotes the surface units which are successively machined during the sweep of the surface of a panel, as well as the areas produced successively by the machining of the same surface unit carried out by successive sweeps of the panel surface. Similarly, "successive sweeps" denotes sweep steps (one step corresponding to a sweep length on the same line) carried out successively to cover the surface of a panel, or sweep steps carried out locally to remove material successively on the same line.

The convergence of the machining toward a defect-free surface state provided by the brightness data of the correlation model is thus achieved by adapting at least one parameter of the variation of depth of machined material, such as the sweep speed, the abrasive flow rate, the sweep step, the electric current for controlling the energy flow, or the pressure provided by the application of energy. This convergence is manifested by a reduction in the difference between the light brightness data of said sweep and the correlation data of the model.

According to some advantageous embodiments:

a comparison between the brightness levels of the surface machined by the preceding sweep and the predetermined typological correspondence data selects and/or updates a typology and speed indexings adapted to this typology for the subsequent sweep;

the indexings of the control parameter of one sweep are compared with the indexings of the preceding sweep, and the stopping of the energy flow can be triggered if a variation of indexing between the sweeps locally exceeds a given maximum difference, preferably if this variation is correlated with a change of brightness level of at least one ply;

the reference value of the control parameter can be modified for a given sweep, starting from the nominal value for the removal of one ply of material as a function of the adjusted indexings for at least one preceding sweep step;

the detection of luminous flux is polarized so as to provide brightness detection having sufficient contrast for the processing of the localized brightness level data, while minimizing the risk of error for different orientations of the light flux.

the stopping of the flow of energy application is triggered if the value of the control parameter is locally adjusted to a value outside a predefined range.

The invention also relates to a system for the ply-by-ply machining of defects of a component made of composite material, adapted to make use of this method. This system includes a numeric data processing unit connected to a sweep control of a machine for applying energy by means of flows in areas to be machined, and an image forming assembly. This assembly includes at least one light source arranged to emit a light flux which can be reflected by a machined surface of the component at not less than two different angles relative to a reference orientation of the fibers of each ply, together with a means for capturing views of the surface of the component illuminated in this way, connected to the data processing unit to provide brightness levels. The processing unit includes means for adjusting the indexing of the local sweep speeds of the component, the speeds varying over a range determined in such a way that the brightness levels of the successive sweeps, provided by the image forming assembly, converge toward a uniformity of brightness correlated with the same depth in terms of "ply units" of the machined area. This "same depth" can be defined as a constant ply depth coinciding with the same interface between two plies.

According to preferred embodiments:

the digital processing unit includes means for comparing brightness levels of the surface machined by the preceding sweep with predetermined typological correlation data, the correlation data and brightness level data after each sweep being stored in memory modules of the processing unit;

a library of models of states of plies of components provides a reference model resembling the component being processed according to the brightness detected after the first sweeps, the model being sent to the typological correlation data memory of the digital processing unit;

the means for capturing views is a digital photographic apparatus, at least two photographs being taken for two angles of orientation of the source correlated with two orientations of ply fibers in the component;

the means for capturing views includes at least one lens fitted with a polarizing filter.

DESCRIPTION OF THE FIGURES

Other data, characteristics and advantages of the present invention will become apparent in the light of the following non-limiting description, relating to the attached drawings, which show, respectively.

DETAILED DESCRIPTION

Figure 1:
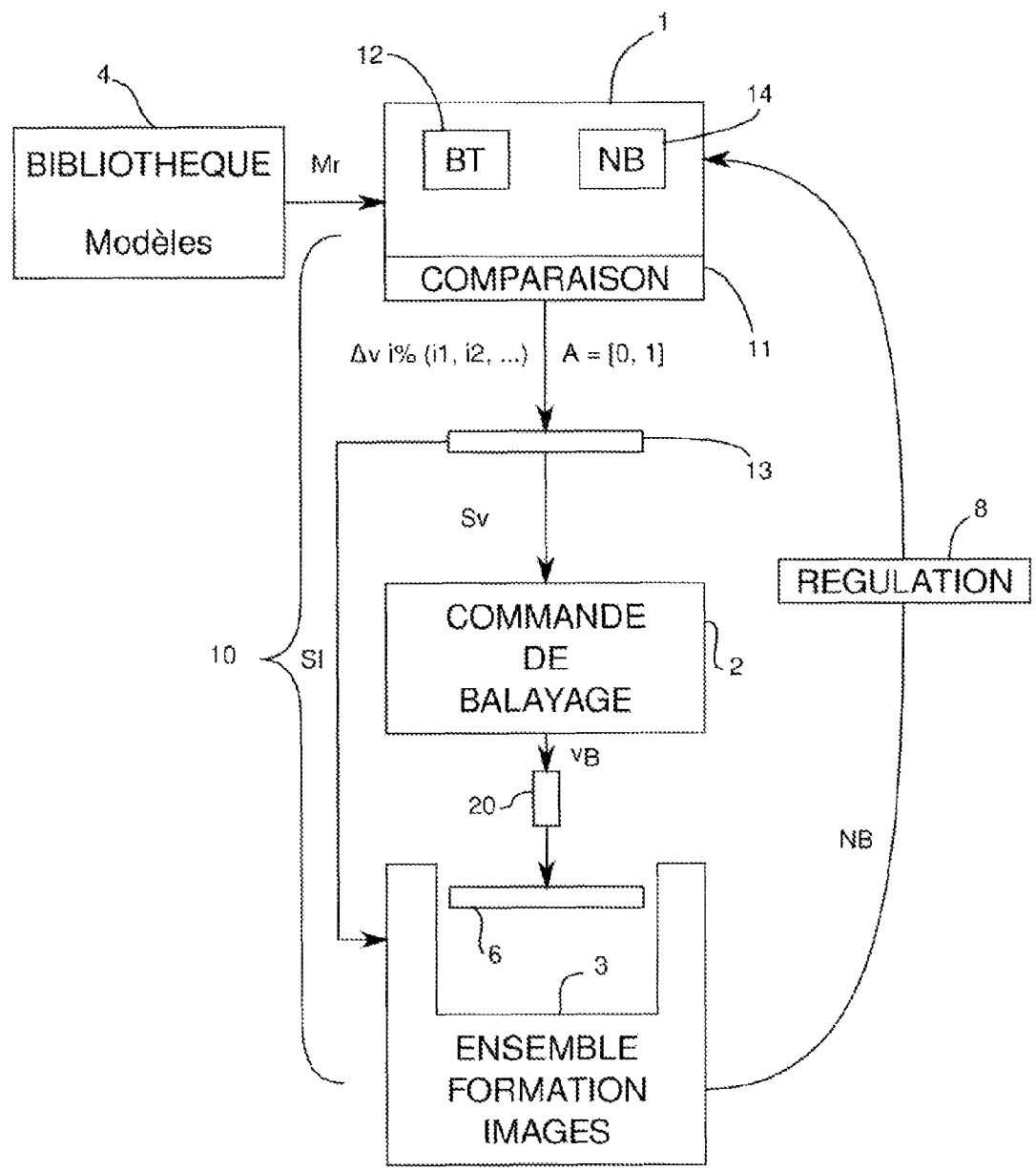
FIG. 1, a functional schematic representation of the system for using the method according to the invention, in the form of a functional diagram.

With reference to the diagram of FIG. 1, a system 10 according to the invention includes a digital data processing unit 1 having a processor and memories. This unit provides a sweep speed signal Sv to a sweep controller 2 of a high-pressure abrasive water jet machine 20. In this non-limiting example, the sweep speed is the parameter used to vary the machining depth. An assembly 3 for forming digital images of a surface of a panel 6 of composite material to be machined is also controlled by means of orientation and light emission signals SI by the digital processing unit 1. This digital image forming assembly 3 supplies brightness levels NB of the illuminated panel surface to the data processing unit 1.

This processing unit 1 delivers indexings with increments of i % for the calculation of the speed signal Sv by adjustment of potentiometers 13. The controller 2 receives the signal Sv and supplies local sweep speed signals $v_B$ to the machine 20. The increments i % (i1, i2, . . . ) are defined as percentages of a reference speed $v_0$, which is theoretically equal to the nominal speed required to remove material corresponding to the depth of one ply, for example 0.2 mm.

However, the reference speed may be modified to allow for the set of increments of speed of a preceding sweep step, in the form of their mean value for example, if this set differs substantially from the nominal value. This reinitialization of the reference speed, which can be performed at each step, makes it possible to follow the variation of the set of increments while continuing to use all the available increments directly for the next step, particularly the extreme increments (200%, 150%; 50%, 30%). This reinitialization therefore makes it possible to avoid additional sweeps which would otherwise have to be provided to achieve a removal of material corresponding to extreme increments which would no longer be directly available.

In the non-limiting examples below, the boundaries for incrementation of the speed $v_B$ are 50% or 30% for the lower boundary and twice the amount (200%) for the upper boundary.

The indexing of the speed signal Sv is, in fact, controlled by the application of a convergent iteration 8 generated by the brightness level data NB provided by the image forming assembly 3, correlated with a depth of removal of material in the preceding sweep. By making a comparison after each sweep between these brightness levels NB and the brightness levels of an identified defect typology correlated with one of the reference models Mr, the processing unit 1 selects the speed increments i % to be applied locally. The brightness/typology correlation data BT and the measured brightness levels NB are stored in data memory modules 12 and 14 of the processing unit 1 and supplied to the comparison means 11.

Advantageously, the speeds indexed for a given sweep are also compared in the comparison means 11 with the speeds that have been indexed in the preceding sweep for the same location. If, for a given panel surface location, the variation in speed indexing is greater than a given maximum difference $\Delta v$, in this case 200% of the reference value $v_0$, a stop signal A to stop the water jet is triggered (A=1). For example, the presence of a large defect may cause the exposure of a ply located two ply units below the machined ply. In this case, the stop signal A stops the abrasive jet for the area concerned.

These comparison means select the speed increments correlated with the degrees of depth in a whole number of plies, of half-plies or of fractions of plies, so that the removal takes place locally in such a way that a ply interface is reached according to the defect typology identified. The convergence is quantified by the corresponding number of sweeps. This determination allows for variations in local speeds $\Delta v$ that are not to be exceeded between two sweeps. Examples of convergence of the brightness levels are given below.

The speed adjustment can be varied to provide a compromise between the precision of the machining, which depends on the dimensions used in the division into areas for machining, and the duration of the operation, by favoring one or other of these or by choosing a middle position between precision and duration. The convergence can be quantified as a number of iterations to be performed, for example on three, four or five sweeps by default, in order to achieve the compromise.

Reference models Mr may be supplied by a library 4 to the memory 12 of the correlations BT with the variable states of brightness of the steps of panels, in accordance with the different types of defect processed. The reference model Mr for the panel to be processed can thus be chosen by comparing the brightnesses provided by the first sweeps. This model may be changed during the processing if a divergence is confirmed by a brightness result which is contrary to the model. The comparison means 11 of the digital processing unit 1 trigger a stop signal A=1 for the system 10 when the divergence is confirmed, for two successive sweeps for example. If the convergence is maintained globally, for example with not more than one divergence in five sweeps, no stop is triggered (A=0).

The brightness of a ply is measured by the luminous intensity of a flux reflected by the ply. This intensity is found by analyzing the light reflected from an image captured by a digital photographic apparatus.

More precisely, the sweep speed is inversely proportional to the amount of material removed, and therefore to its depth. The speed range is therefore directly related to the range of ply depths which can be removed by the current sweep, this range therefore extending, in the example described below, between ½ and 2 plies when the speed varies, respectively, between twice and half the reference speed.

The sweep speed $v_B$ is then indexed locally by one of the increments $i_1, i_2, \ldots$, (expressed in %), classed in decreasing order according to predetermined ply configurations. For a current sweep $B_n$, the comparison between configuration data, particularly the brightness levels NB of the preceding sweep $B_{n-1}$ and the predetermined typological correlation data BT, enables the processing unit 1 to select a typology for the current sweep and to update it if it has already been selected, and to select the speed indexings $v_B$ that are most suitable for the selected or updated typology.

The configuration data relate to the brightness level NB of the surface and, preferably, also to the sweep data, particularly the speed increments indexed in the preceding sweep or sweeps. Advantageously, other more precise data on the depth of removal in the ply to which the current sweep relates allow the selection to be refined on the basis of a larger number of increments. These depth data are, for example, provided by a 3D laser scanner. In this case, the correlation data relate to correlations between brightness and typology, BT. These BT data are advantageously supplemented during the operation by the machining history which corrects the selected typology or changes the typology.

The indexing of the speed increments is determined by the degree of precision acquired in the course of the machining. The speed is initially indexed to the maximum increment $i_1$, in order to remove the minimum amount of material. This situation is the result of imprecise brightness level information NB which, compared with the brightness/typology correlation data BT—at the start of processing, for example—does not allow the processing unit 1 to set this value to a finer increment. However, during the machining of the plies, the sweep speed progressively uses adjusted increments, closer to 100% for example, because the successive comparisons of brightness levels allow the machining depth to be adjusted more accurately so as to tend toward the same interface between plies.

The sweep speed $v_B$ then converges globally incrementally toward the nominal speed $v_0$ so that the machining can be continued ply-by-ply: the difference between the sweep speed and the nominal speed tends globally toward 0 for each defect.

Figure 2:
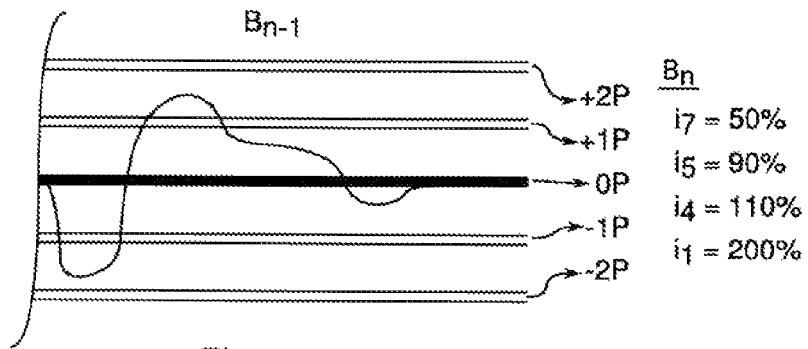
FIG. 2, a schematic sectional view of a sweep profile for an example of machining of plies of a panel as a function of a ply interface to be reached.

In the example of machining illustrated in the schematic cross section of FIG. 2, the profile denoted $B_{n-1}$ is that of the preceding sweep. It corresponds to a removal of material from the plies to increasing depths +2P, +1P and −1P, −2P, identified, respectively, above and below the interface 0P between the plies +1P/−1P, which is the standard interface level to be reached after an appropriate additional number of sweeps for the correction of the defect by successive machining. The plies have been identified by their brightness level, ply-by-ply, without the use of more precise data on the degrees of depth of removal of material in each ply.

The brightness analysis of the sweep profile $B_{n-1}$ indicates machining depths at the ply level −2P, +2P, +1P and −1P. The sweep speed for the sweep to be performed in the next sweep $B_n$ is adjusted:

at the level of ply −2P, by the highest increment, in this case $i_1$=200%, so as to remove the least possible amount of material in order to approach the target interface as fast as possible;

at the level of ply −1P, the speed is incremented by a value greater than the nominal speed, for example $i_4$=110%, so as to remove less than one ply's depth in order to reach the interface;

for levels +2P and +1P, the speed is indexed by increments of less than 100% of the nominal speed, so as to remove more than one ply's depth of material: at level +2P, the speed is incremented by $i_7=50\%$, and at level +1P it is incremented by $i_5=90\%$ of the nominal speed.

During the operation, the brightness data NB compared with the typology correlation data BT (FIG. 1) enable the reliability of the method to be increased by using the most suitable increment at each sweep. The processing unit 1 then generates sweep speed control signals Sv which tend toward the reference speed signal $v_0$ with indexings with successive increments converging globally toward 100%.

If the brightness data are combined with ply depth data, provided by the 3D laser scanner for example, the degree of ply depth removed is quantified by half-plies or ply fractions. The adjustment of the sweep speed can then be refined by multiplying the number of increments corresponding to these ply fractions. The number of plies required for convergence is globally reduced.

For example, the sweep speed, which is incremented at the start of the operation by a single high value of 200% for the detection of a ply having a level once (such as −1P) or twice (such as −2P) as low as the reference level 0P, is assigned, respectively, according to a plurality of values adjusted in the course of operation for the same plies, namely: $i_1=200$, $i_2=150$, $i_3=130$ and $i_4=110\%$ for the detection of a ply at a level twice or once as low; $i_5=90\%$, $i_6=70$, $i_7=50$ and $i_8=30$, for the detection of a ply at a level once or twice as high. All these values are preset in the processing unit 1.

Figure 3:
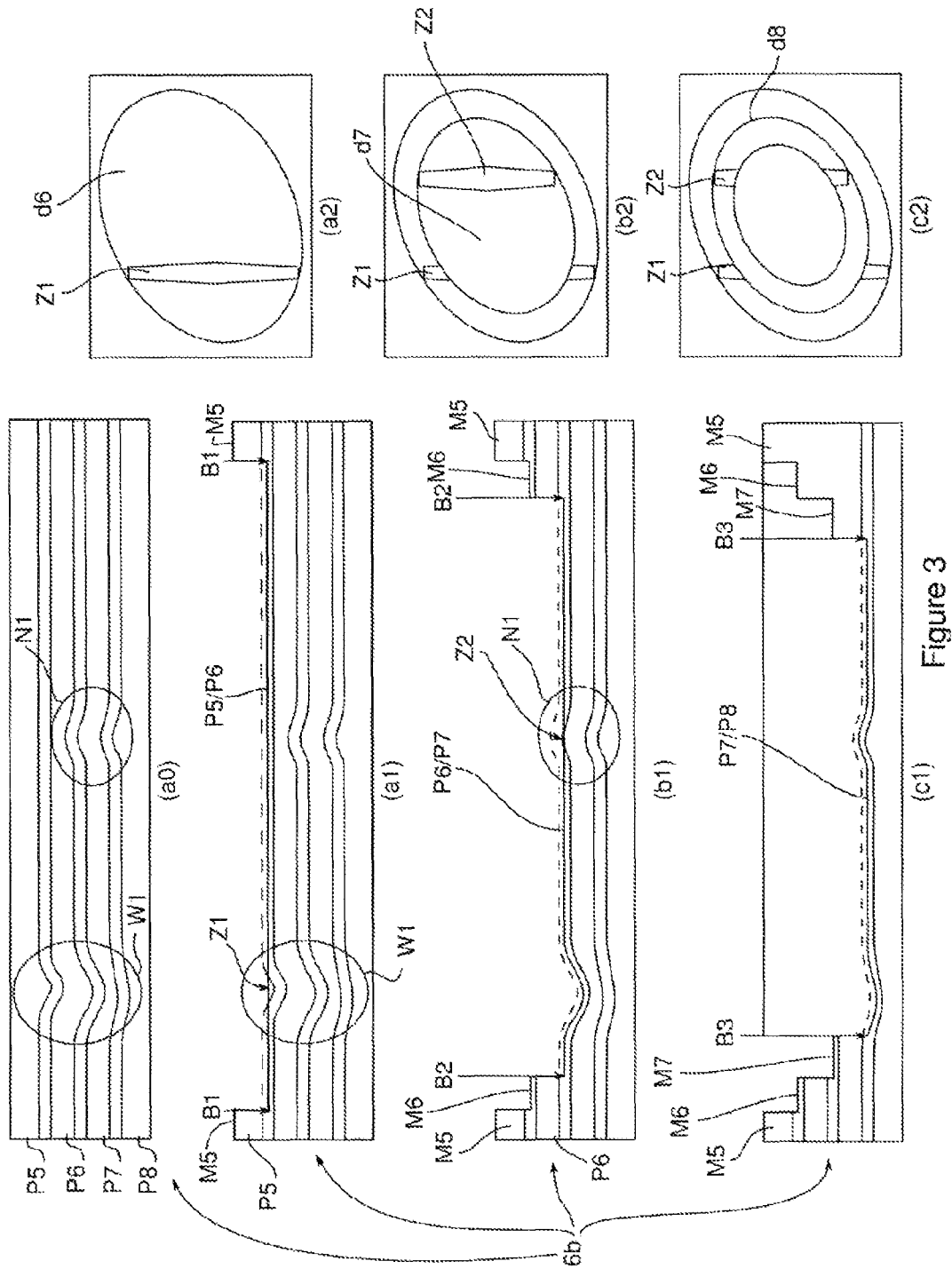
FIG. 3, a first sectional diagram (a0) of a panel of composite material before processing and sectional diagrams (a1), (b1), (c1) and top views (a2), (b2), (c2) of this panel in a simplified example of processing according to the invention to a depth of three plies.

In the context of defects of the "wrinkle" or "rib" type, the diagram (a0) in FIG. 3 shows a sectional view of a panel 6b of composite material. Plies P5 to P8 of this panel 6b include defects in the form of a wrinkle W1 and a rib N1. Diagrams (a1, a2) to (c1, c2) of FIG. 3 show, respectively, sectional and top views of the panel 6b in a simplified example of processing according to the invention. The processing is based on the recognition of the plies and the monitoring of the defects over a depth forming concentric stages in four plies.

In diagram (a1), a first sweep B1 of the abrasive water jet at constant speed v1 eliminates the first ply P5 to a constant depth in the form of a central disk, forming a step M5. At least one defect has been detected by a first image brightness analysis and a choice of reference model has been made for this defect. The top view diagram (a2) shows more clearly the central disk d6 of the interface of plies P5/P6 corresponding to a first removal of material from ply P5.

The brightness analysis identifies an area Z1 having a different brightness from the rest of the disk d6 and corresponding typologically to the presence of a wrinkle W1 formed in the plies. Because of this defect, the first ply P5 has not completely disappeared locally in the area Z1 during the constant-depth machining of the first ply P5.

The second sweep B2 (diagrams b1, sectional, and b2, top view) forms a recess with concentric stages (steps M5 and M6) and takes into account the teachings provided in the first sweep B1: the digital processing unit 1 (FIG. 1) compares the brightness of the area Z1 of the first sweep B1 with that of a stored wrinkle model W1 of the same type. The successive state of the plies of this wrinkle corresponding to this brightness is thus identified. This state implies that the remaining degree of depth of ply P5 as identified by its brightness is about 10%, and that the deformation of the next ply is probably about 30%. The processing unit 1 then indexes the speed to 70% of nominal speed (indexing $i_6$), to be applied to the second sweep B2 when the abrasive water jet is positioned precisely over the area Z1, in connection with the sweep controller 2 (see FIG. 1). This area is machined and the whole of ply P6 is eliminated in a central disk sweep area d7. After a check has been made to ensure that ply P6 has indeed been eliminated because of the uniform brightness level, the indexing is adjusted to 100% of the nominal speed $v_0$.

On the other hand, the second sweep B2 reveals a new area Z2 whose brightness contrasts with that of the rest of the central disk d7 corresponding to the interface of plies P6/P7, the disk d6 now appearing in the form of a ring (diagram b2). By comparing the brightness with a model of a rib defect N1, and allowing for the difference between the brightness of the area Z2 and that of the area Z1 of the defect W1, the processing unit identifies the state of the corresponding ply P and the presence of fibers of the ply P7 in this area Z2. On the other hand, the interface P6/P7 has clearly been reached, because the brightness has disappeared in the disk d7.

These teachings are used in the speed indexing of the third sweep B3 (diagrams c1 and c2). The processing unit indexes a speed of 110% (increment $i_4$) for the removal of the whole of ply P7 over a depth of less than one ply in the area of the wrinkle W1, because the wrinkle model predicts a reduction of the defect of this order of magnitude. It also predicts a sweep speed indexed at 110% to be applied over a depth of less than one ply when the abrasive water jet is positioned over the area Z2, so as to reach and remain in the interface of plies P7/P8. After the completion of the third sweep, the central disk d8 (diagram c2) corresponds to the interface of plies P7/P8, without any apparent defect.

Figure 4:
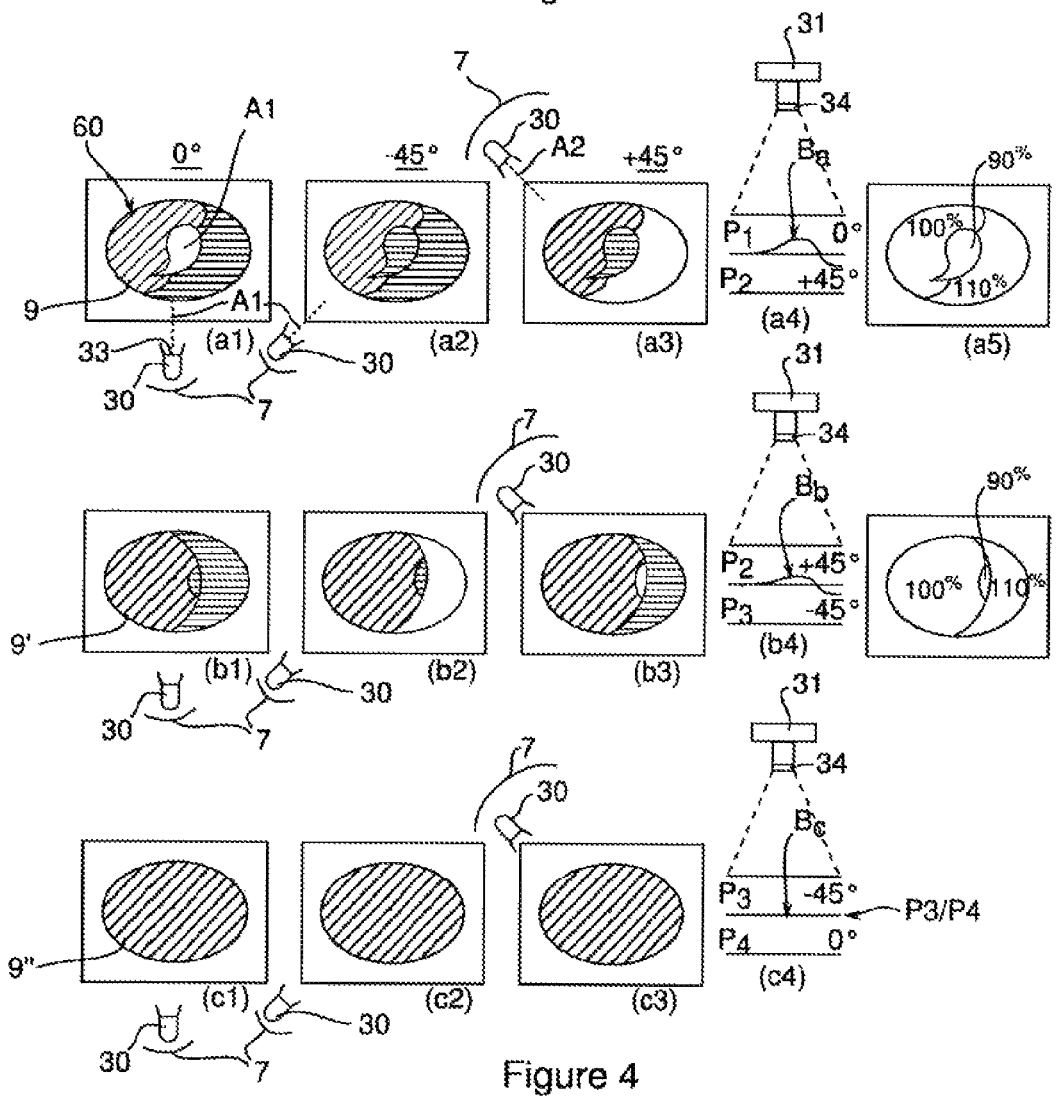
FIG. 4, schematic top views (a1 to a3, b1 to b3, c1 to c3) of an example of ply machining of a panel by three successive sweeps, accompanied by diagrams of the sweep profiles (a4, b4, c4) and correlated sweep speed indexings (a5, b5)

Diagrams (a1)) to (a3), (b1) to (b3) and (c1) to (c3) of FIG. 4 show, in a simplified example, the monitoring of the brightness levels NB for ply recognition. The brightness levels of a surface of a panel of composite material 60 are monitored for three machining sweeps respectively, and at three exposure angles for each sweep, namely 0°, −45° and +45°. After reaching the interface between plies P3/P4, the machining is continued ply-by-ply, using the same method, after the elimination of the defect extending through plies P1 to P3. For simplicity, this convergence is produced by performing these three sweeps. The diagrams (a4), (b4) and (c4) show in sectional views the sweep profiles, the capture of views by a photographic apparatus 31, and the plies successively machined after each of the three successive sweeps Ba, Bb and Bc. Additionally, the diagrams (a5) and (b5) show the speed increments indexed for sweeps Bb and Bc.

The image forming assembly includes a light source 30 mounted on a rotating support 7 and a digital photographic apparatus 31 located above the panel. To improve the accuracy of detection of the orientation of the fibers of the plies, the lens is fitted with a polarizing filter 34 mounted on a rotating ring (not shown). This detection is then sufficiently accurate to define brightness areas (see below) at each sweep, making it possible to carry out extremely fine machining for the repair or correction of defects.

This photographic apparatus 31 is positioned above the surface of the panel 6 so that its optical axis A1 is perpendicular to the panel 6. The source 30, its optical axis A2 and the luminous flux 33 emitted from the source 30 are oriented successively in the three directions 0°, −45° and +45° after each sweep. The successive increasingly deep plies—P1, P2, P3 and P4—are oriented according to the sequence 0°/+45°/−45°/0° with respect to the same angular reference as that used to identify the directions of the source 30.

With reference to diagrams (a1) to (a3), it appears that the sweep has not removed all of ply P1: a portion of the upper ply P1, which reflects the luminous flux 33 oriented at 0°, is visible in diagram a1. Diagram a2 shows that no ply with an orientation of −45° is present at this sweep level. For its part, ply P2 is identified by the reflection of the luminous flux 33 oriented at +45° (diagram a3). A band of gray resin 6, located at the interface of the plies P1/P2 (diagram a4), also appears regardless of the orientation. Diagram a4 clearly confirms the coherence between the reflections formed by the plies P1, P2, as well as their interface P1/P2 and the track of the sweep Ba between plies P1 and P2.

At this stage, the objective of converging the machining toward an interface of the plies has not been achieved. In order to tend toward this objective, the sweep speeds of the next sweep Bb (diagram b4) are indexed by the increments (diagram a5) which enable the degree of the depth of removal of material to be modulated as a function of the position of the ply above or below an interface.

For the upper ply P1, the speed is indexed by an increment $i_5$=90% corresponding to a speed below the nominal speed for removal of one ply. A removal of material which is greater (by about 10%) than that corresponding to the depth of one ply is therefore provided. This indexing will make it possible to approach the next interface P2/P3 more closely (diagram b4) after the next sweep.

For the lower ply P2, the speed is indexed by an increment $i_4$=110%, corresponding to a higher speed; the predicted degree of depth of removal of material is less than one ply, so that said next interface P2/P3 can be approached in the next sweep.

As regards the extent of resin 9 located at the P1/P2 interface, machining with a degree of depth equal to one ply should be maintained, in order to reach the P2/P3 interface. Indexing the sweep speed to the nominal speed (100% indexing) enables this interface to be reached during the next sweep Bb.

After the execution of this sweep Bb, according to the speed increments shown in diagram a5—namely 100% (machining between interfaces), 90% (machining of ply P1) and 110% (machining of ply P2)—the resulting machining is identified by the brightness of the surface 60 as photographed at the orientations 0°, −45° and +45°, according to diagrams b1 to b3.

In these diagrams, it is clear that the machining has made it possible to tend toward the P2/P3 interface: the extent of the resin 9' is substantially greater than the extent of the resin 9 on the upper P1/P2 interface (diagrams a1 to a3), because of the adaptation of the sweep speeds by appropriate increments (90% and 110%) enabling the machining of plies P2 and P3 to partially "rectify" the P2/P3 interface in question. As a corollary, the extent of plies P2 and P3 revealed by the orientation of the luminous flux 33 at −45° (diagram b2) and +45° (diagram b3) is smaller than that of plies P1 and P2 of the preceding sweep (diagrams a1 and a3). These variations are also manifested in the profile of the sweep Bb (diagram b4) which approaches the P2/P3 interface.

The indexings of the sweep speeds are maintained for the next sweep Bc (diagram b5), at 100% (machining of the interface P2/P3), 90% (machining of ply P2) and 110% (machining of ply P3).

The execution of the sweep Bc enables the machining to converge toward the P3/P4 interface: in addition to the machining by one ply (100% indexing on the nominal speed) of the P2/P3 interface which leads to the P3/P4 interface, the machining of ply P2 with a sweep speed below the nominal speed (indexing at 90%)—resulting in machining over a degree of depth greater than that of one ply—also enables the P3/P4 interface to be reached. Similarly, the machining of ply P3 with a sweep speed greater than the nominal speed (indexing at 110%)—resulting in machining over a degree of depth less than that of one ply—enables the P3/P4 interface to be reached.

Diagrams c1 to c3 show that, regardless of the orientation of the luminous flux 33, the same reflection of resin 9" at the P3/P4 interface is obtained. The machining profile of the sweep Bc as illustrated by diagram c4 clearly confirms the positioning of this profile on the P3/P4 interface.

In some cases, the machining may itself cause the appearance of singularities that must be eliminated. One known case is that of curved panels, such as the panel 6d shown in FIG. 5, seen in section in diagram (a) and in a partial top view in diagram (b). The principle of machining by applying energy from a source moving at a constant distance, for example by a water jet with a flow F1 from a nozzle S1 moving in a plane $P_F$, causes a progressive offset of the machining when the machining is carried out on inclined parts. This is because the depth of machining is constant, for example over a nominal depth Ep of one ply. A defect of non-removed material D4 is then formed at an end "E" of the panel 6d during the removal of the first ply Pa by a first sweep Bi of an abrasive water jet. The top view (b) shows the retention of the ply Pa over a large part of the surface, outside the Pa/Pb interface.

Figure 5:
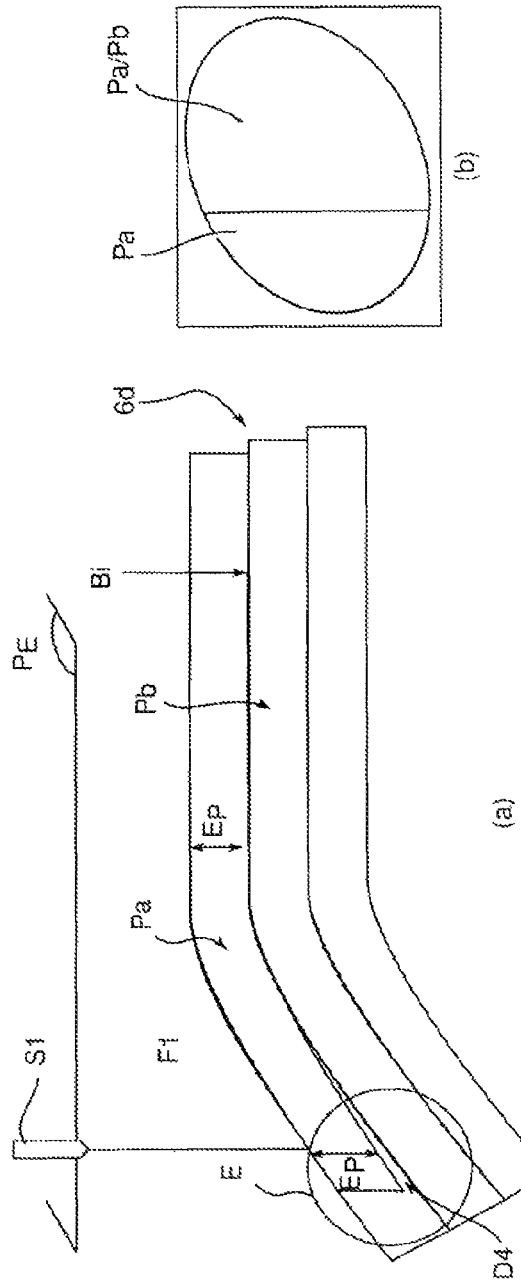
FIG. 5, a sectional view (a) and a top view (b) of a composite panel with a curved edge processed conventionally with a first sweep at constant speed.
Figure 6:
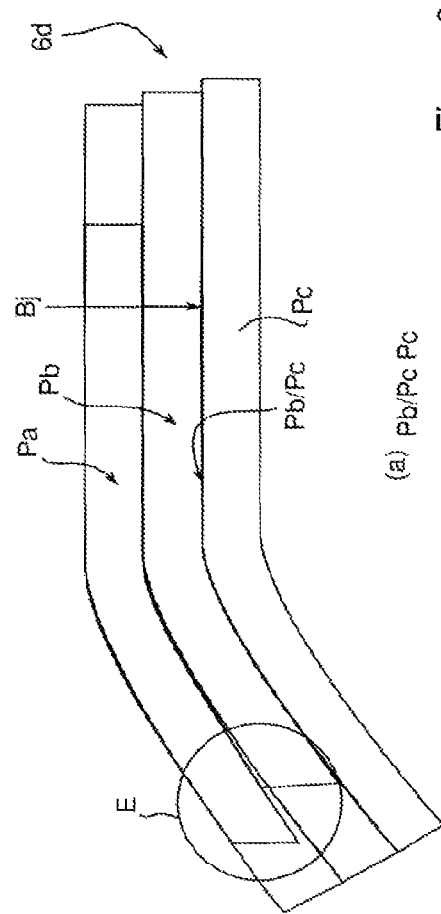
FIG. 6, a sectional view (a) and a top view (b) of the composite panel with a curved edge of FIG. 5, processed according to the invention with a second sweep at variable speed.

The invention corrects this defect according to FIG. 6, which repeats the views of diagrams (a) and (b) of FIG. 5 in the context of the invention. The second sweep Bj "erases" the defect at the end "E" by reducing the speed by incrementation of 90% of the nominal sweep speed at this end "E". In this way, more than one ply's depth of material is removed in order to compensate for the insufficient removal of material in the preceding sweep. Consequently, the central disk d9 of the interface of plies Pb/Pc (top view (b)) no longer shows a defect.

The invention is not limited to the exemplary embodiments described and illustrated. The method according to the invention may be fully automated, semi-automated or partially automated, or may remain manual, for example by using observation by an expert operator instead of a photographic apparatus. Thus the reference models may be empirical models based on the visual experience of brightnesses. The energy application system may also be different from a high-pressure abrasive water jet. For example, laser or ultrasonic systems may be used.

It is also possible to provide a camera or photographic apparatus attached to the machine for emitting the energy flow. In this case, the brightness levels may be monitored locally in elementary areas whose dimensions are as small as is technologically possible. The speed indexings can then be adjusted for each elementary area with an adjusted removal of material.

The invention claimed is:
1. A method for a ply-by-ply machining of singularities (W1; N1; D4) of a component (6, 6b, 6d) made of composite material, composed of a stack of plies (P1 to P4; P5 to P8; Pa to Pc), the method comprising the steps of:
applying energy in a flow by an area-by-area sweeping of the component to be machined;
detecting at least one light flux (33) reflected from areas (Z1, Z2; 60) machined by sweeping the component (6, 6b, 6d) providing local brightness levels (NB) correlated with ply orientations
indexing at least one parameter ($v_B$) for controlling a variation of depth of a material to be machined in a machine for applying energy (20) as a function of the plies of the component (6) detected in the swept areas (Z1, Z2; 60) by their brightness level (NB) and of their relative position with respect to an inter-ply interface level (0P, P2/P3, P3/P4); and
calibrating the indexing by predefined increments (i1 to i4; i5 to i8) in a range including a reference value (v0) and correlated with degrees of depth of removal of the mate- rial, so that the brightness levels of successive sweeping converge toward a uniformity of brightness when the ply is constant.

2. The method for ply-by-ply machining as claimed in claim 1, wherein the control parameter is chosen from among the sweep speed ($v_B$), the abrasive flow rate, the sweep step, the electric current controlling the energy flow, and the pressure provided by the application of energy.

3. The method for ply-by-ply machining as claimed in claim 2, wherein, for each sweep, a comparison between the brightness levels (NB) of the surface machined by the preceding sweep ($B_{n-1}$) and the predetermined typological correlation data (BT) selects and/or updates a typology and speed indexing adapted to this typology for the subsequent sweep ($B_n$).

4. The method for ply-by-ply machining as claimed in claim 1, wherein the indexing of the control parameter of a given sweep ($B_n$) are compared with the speed indexing of the preceding sweep ($B_{n-1}$), and the stopping (A) of the energy flow can be triggered if a variation of indexing between the sweeps locally exceeds a given maximum difference, preferably if this variation is correlated with a change of brightness level of at least one ply.

5. The method for ply-by-ply machining as claimed in claim 1, wherein the reference value ($v_0$) of the control parameter can be modified for a given sweep, starting from the nominal value for the removal of one ply of material as a function of the adjusted indexing for at least one preceding sweep step.

6. The method for ply-by-ply machining as claimed in claim 1, wherein the detection of luminous flux (33) is polarized (35) so as to provide brightness detection having sufficient contrast for the processing of the localized brightness level data (NB), while minimizing the risk of error for different orientations (−45, 0, +45) of the light flux (33).

7. An optimized repair method as claimed in claim 1, wherein the stopping (A) of the flow of energy application is triggered (A=1) if the value of the control parameter is locally adjusted to a value outside a predefined range.

8. A system for the ply-by-ply machining (10) of defects (W1; N1) in a component (6, 6b, 6d) made of composite material, adapted to apply the method as claimed in claim 1, wherein includes a digital data processing unit (1) connected to a sweep controller (2) of a machine for applying energy (20) in flows in the areas to be machined, and an image forming assembly (3) including at least one light source (32) arranged to emit a light flux (33) that can be reflected by a machined surface (60) of the component (6, 6b, 6d) at not less than two different angles (−45°, 0°, +45°) with respect to a reference orientation of the fibers of each ply (−1P, −2P, +1P, +2P; P1 to P4), together with a views capturing device (31) of the surface (60) of the component (6, 6b, 6d) illuminated in this way, connected to the data processing unit (1) to provide brightness levels (NB), and in that the processing unit (1) includes an adjusting device (11, 13) for the indexing of the speeds of local sweeps of the component (6, 6a, 6b), the speeds varying within a predetermined range (Δv) so that the brightness levels (NB) of the successive sweeps, provided by the image forming assembly (3), converge toward a uniformity of brightness correlated with the same depth in "ply units" (0P, P2/P3, P3/P4) of the machined area.

9. The system for ply-by-ply machining (10) as claimed in claim 8, wherein the digital processing unit (1) includes a device for comparing (11) brightness levels (NB) of the surface machined by the preceding sweep ($B_{n-1}$) with predetermined typological correlation data (BT), the correlation data (BT) and brightness level data (NB) after each sweep being stored in memory modules (12, 14) of the processing unit (1).

10. The system for ply-by-ply machining as claimed in claim 8, wherein a library (4) of models of states of plies of components provides a reference model (Mr) resembling the component being processed according to the brightness detected after the first sweeps, the model (Mr) being sent to the typological correlation data (BT) memory (12) of the digital processing unit (1).

11. The system for ply-by-ply machining as claimed in claim 8, wherein the views capturing device is a digital photographic apparatus (31), at least two photographs being taken for two angles of orientation of the light source (31) correlated with two orientations of ply fibers in the component (6).

12. The system for optimizing repairs as claimed in claim 8, wherein the views capturing device includes at least one lens fitted with a polarizing filter (34).

* * * * *